United States Patent [19]

Berkelhammer et al.

[11] 4,178,460

[45] Dec. 11, 1979

[54] 2-HALOALKYL(OXY-, THIO-, SULFINYL-, OR SULFONYL)-PHENYLALKANOIC ACIDS

[75] Inventors: Gerald Berkelhammer, Princeton; Venkataraman Kameswaran, Princeton Junction, both of N.J.

[73] Assignee: American Cyanamid Co., Stamford, Conn.

[21] Appl. No.: 890,721

[22] Filed: Mar. 20, 1978

Related U.S. Application Data

[63] Continuation-in-part of Ser. No. 830,515, Sep. 6, 1977, abandoned, which is a continuation-in-part of Ser. No. 728,817, Oct. 1, 1976, abandoned.

[51] Int. Cl.² .................... C07C 65/02; C07C 149/40; C07C 147/107; C07C 147/14
[52] U.S. Cl. .................... 562/426; 260/465 D; 260/465 F; 260/465 G; 260/609 R; 560/9; 560/11; 560/12; 560/13; 560/22; 560/23; 560/55; 562/401; 562/429; 562/430; 562/437; 562/438; 562/465; 562/478; 568/655; 424/304; 424/308; 424/309
[58] Field of Search ............... 562/429, 465, 426, 430, 562/437, 438

[56] References Cited

U.S. PATENT DOCUMENTS

| | | | |
|---|---|---|---|
| 3,632,629 | 1/1972 | Bulteau | 562/429 |
| 3,729,508 | 4/1973 | Ziegler et al. | 562/429 |
| 3,766,244 | 10/1973 | Giacobbe et al. | 562/426 |

FOREIGN PATENT DOCUMENTS 1174535 12/1969 United Kingdom .................... 562/465

*Primary Examiner*—Jane S. Myers
*Attorney, Agent, or Firm*—H. G. Jackson

[57] ABSTRACT

The invention is 2-haloalkyl(oxy-, thio-, sulfinyl-, or sulfonyl)phenylalkanoic acids which are useful intermediates in the preparation of insecticides of m-phenoxybenzyl and α-cyano-m-phenoxybenzyl esters.

13 Claims, No Drawings

2-HALOALKYL(OXY-, THIO-, SULFINYL-, OR SULFONYL)-PHENYLALKANOIC ACIDS

This application is a continuation-in-part of copending application Ser. No. 830,515 filed Sept. 6, 1977 now abandoned which in turn is a continuation-in-part of now abandoned application, Ser. No. 728,817, filed Oct. 1, 1976.

Insecticidal esters made from the compounds of this invention are claimed in our copending application, Ser. No. 814,600, filed July 11, 1977 now abandoned.

The closest art of which we are aware is disclosed in South African Patent Application No. 73/4462 which teaches phenylacetic acid derivatives of the formula:

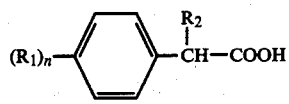

including alkoxy phenylacetic acids which are useful intermediates to prepare insecticidal phenylacetic acid esters. See also Belgian Pat. No. 650,701.

The invention is 2-haloalkyl(oxy-, thio-, sulfinyl-, or sulfonyl)phenylalkanoic acids of the formula:

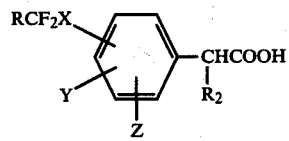

wherein $RCF_2X—$, Y and Z are all meta or para to the carbon to which the alkanoic acid group is attached; R is H, F, Cl $CHF_2$, or $CF_3$; X is O, S, SO or $SO_2$; $R_2$ is ethyl, n-propyl, isopropyl, isopropenyl or t-butyl; and Y and Z are H, Cl, F, Br, $NO_2$, $CH_3$, or $OCH_3$. Preferred compounds of the invention are compounds wherein X is S or O. The compounds are useful intermediates in the preparation of the m-phenoxybenzyl and α-cyano-m-phenoxybenzyl esters.

The acids VIII of the invention shown in the Flow Diagram below where $R_2$ is ethyl, n-propyl, or isopropyl, can be prepared using the appropriate toluene (IV) as a starting material. The process for the preparation involves four steps, the first of which is the halogenation of the toluene (IV) with bromine, chlorine, N-bromosuccinimide (NBS), or the like. This reaction is preferably conducted in the presence of an inert organic solvent such as carbon tetrachloride, and a radical initiator such as light, benzoyl peroxide, or azo-bis-isobutyronitrile, to yield the benzyl halide (V). The formula V benzyl halide is then converted to the corresponding phenylacetonitrile (VI) by reaction with sodium or potassium cyanide in the presence of dimethylsulfoxide (DMSO), ethanol, or the like, at an elevated temperature. Alternatively, the benzyl halide may be reacted with sodium or potassium cyanide in an aqueous toluene mixture using a quaternary ammonium salt such as benzyl triethylammonium chloride or tricapryl methylammonium chloride or a tertiary amine such as tri-n-hexylamine or a crown ether. This (substituted phenyl)acetonitrile (VI) is then readily alkylated when treated with an alkyl halide in the presence of base and an inert organic solvent; crown ethers have been found to be useful catalysts in this reaction. The α-alkyl(substituted phenyl)acetonitrile formed in the above reaction is depicted by formula VII and hydrolysis of this formula VII α-alkyl(substituted phenyl)acetonitrile, using an alkali metal hydroxide in the presence of an alkylene glycol and water, yields the alpha-alkyl(substituted phenyl)acetic acid, shown as formula VIII. Treatment of the formula VIII acid with thionyl chloride, thionyl bromide, or the like, preferably in the presence of an aromatic solvent such as benzene or toluene, then yields the alpha-alkyl(substituted phenyl)acetyl halide (II), which is reacted with the m-phenoxybenzyl alcohol (III, $R_3=H$) or alpha-cyano-m-phenoxybenzyl alcohol (III, $R_3=CN$) to yield the desired m-phenoxybenzyl ester or alpha-cyano-m-phenoxybenzyl ester of the 2-haloalkyl(oxy-, thio-, sulfinyl-, or sulfonyl)-phenylalkanoic acids (I) which are useful insecticides.

These reactions are graphically illustrated in Flow Diagram I below.

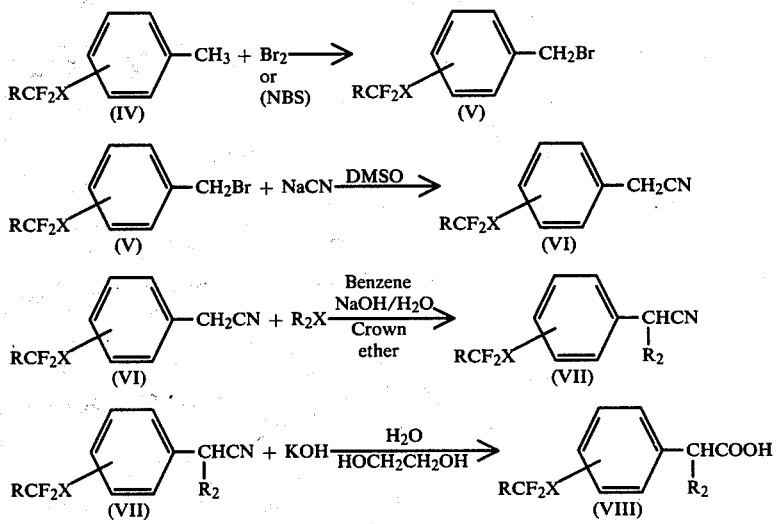

FLOW DIAGRAM I
Preparation of 2-Haloalkyl(oxy-, thio, sulfinyl-, or sulfonyl)-phenylalkanoic Acids.

FLOW DIAGRAM I
Preparation of 2-Haloalkyl(oxy-, thio, sulfinyl-, or sulfonyl)-phenylalkanoic Acids.

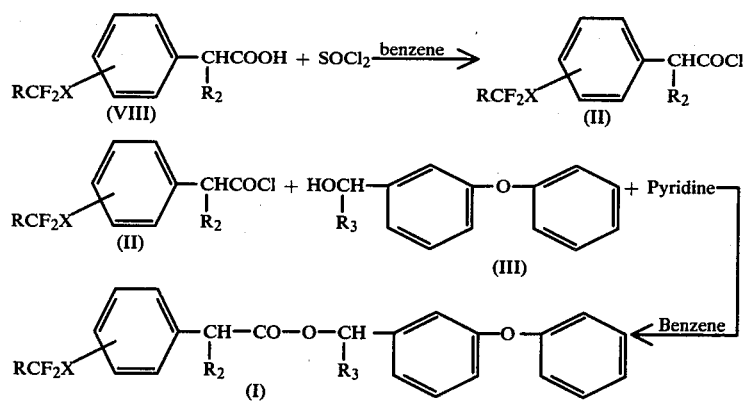

As as alternative to the benzyl bromide (V), shown in Flow Diagram I, where products are to be limited to para-substitution, the appropriate haloalkyl(oxy- or thio-)benzene (IX) may be chloromethylated using a mixture of para-formaldehyde or trioxane with zinc chloride and dry hydrogen chloride to afford the benzyl chloride (X) which can then be used in place of V for completion of the synthesis to VIII. This modification is illustrated as follows:

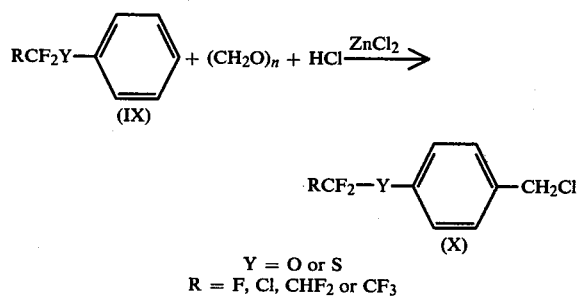

Y = O or S
R = F, Cl, CHF$_2$ or CF$_3$

Preparation of the α-alkyl-3(or 4)-trifluoromethoxyphenyl acetic acid can also be accomplished by a sequence beginning with the alkylation of m- or p-methoxyphenylacetonitrile, using an alkyl halide in the presence of a crown ether and base. It is, of course, obvious that when the m-methoxyphenylacetonitrile is used in this reaction the α-alkyl-3-methoxyphenylacetonitrile is obtained, and when the p-isomer is employed the α-alkyl-4-methoxyphenylacetonitrile is obtained. It will, likewise, become apparent from the following discussion that the location of the methoxy group on this phenylacetonitrile starting material determines the position of the trifluoromethoxy substituent in the final product.

The α-alkyl-3(or 4)-methoxyphenylacetonitrile, referred to above, is converted to the α-alkyl-3(or 4)-hydroxyphenylacetonitrile by treatment with boron tribromide, preferably in the presence of a solvent such as methylene chloride. Treatment of the thus-formed phenol with thiophosgene and base in the presence of a solvent such as chloroform, then yields the chlorothio ester of O[m- or p-(1-cyano-2-methylpropyl)phenyl]formic acid. This ester is converted to the α-alkyl-3(or 4)-trifluoromethoxyphenylacetonitrile with molybdenum hexafluoride, and this compound is then hydrolyzed to the corresponding α-alkyl-3(or 4)-trifluoromethoxyphenylacetic acid by reaction with ethylene glycol in the presence of an alkali metal hydroxide and water.

These reactions are graphically illustrated in Flow Diagram II below.

FLOW DIAGRAM II

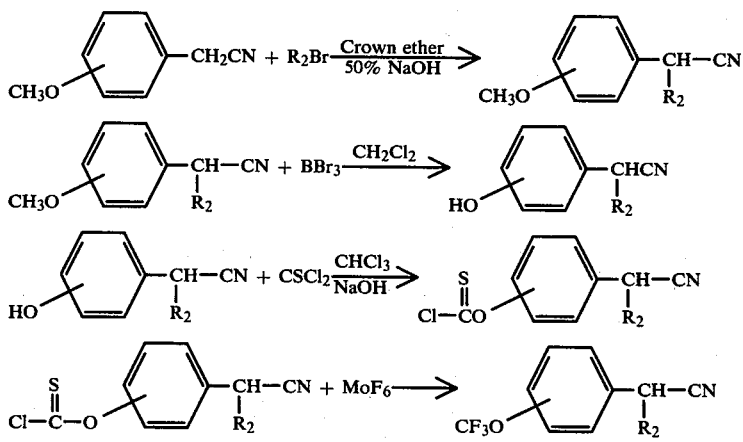

FLOW DIAGRAM II

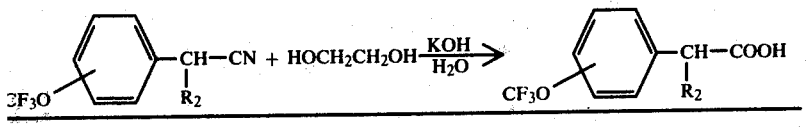

In the reactions set forth on Flow Diagram II, $R_2$ is ethyl, n-propyl or isopropyl.

Whereas Flow Diagram I has general application for the preparation of many compounds of this disclosure as described, it is found that in the alkaline hydrolysis of the nitriles for those examples in which $RCF_2X-$ is $HCF_2O-$ or $HCF_2S-$ that the $HCF_2-$ radical can be lost. However, we have found that it may be reintroduced by reacting the appropriate phenol or thiophenol with chlorodifluoromethane in a mixture of aqueous alkali and dioxane.

The actual synthesis of those examples incorporating the $HCF_2O-$ group is best demonstrated by the Flow Diagram III in which the appropriate α-alkyl-3(or 4)-methoxyphenylacetonitrile (as shown in Flow Diagram II) is converted to the α-alkyl-3(4)-hydroxyphenylacetic acid using hydrobromic acid. Treatment with chlorodifluoromethane in aqueous alkali and dioxane affords the α-alkyl-3(4)-difluoromethoxyphenylacetic acids.

FLOW DIAGRAM III

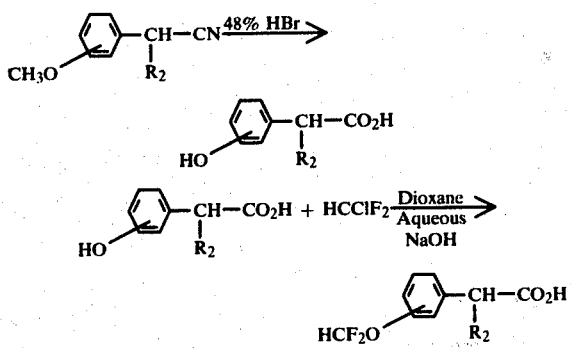

It is also to be noted that although the procedure outlined in Flow Diagram I is suitable for the preparation of most examples where

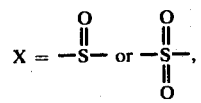

it is frequently better to prepare the final acids (VIII) in which $X=-S-$ and then to oxidize the sulfur atom to the desired

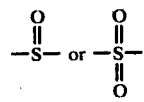

analog through the use of appropriate oxidizing agents such as m-chloroperbenzoic acid, sodium periodate, or hydrogen peroxide.

To prepare those compounds of structure VIII in which $R_2$ is t-butyl, the following reaction sequence is used, starting with appropriate meta- or para-substituted aldehyde:

(1) reaction with t-butyl magnesium chloride;
(2) conversion of the neopentyl alcohol to the chloride using thionyl chloride;
(3) preparation of the Grignard reagent from the chloride using magnesium in tetrahydrofuran; and
(4) carboxylation with carbon dioxide.

The sequence is further exemplified by the synthesis of α-t-butyl-3(or 4)-trifluoromethoxyphenylacetic acid as illustrated in Flow Diagram IV. The acids can be converted to the corresponding esters, as illustrated in Flow Diagram I.

FLOW DIAGRAM IV

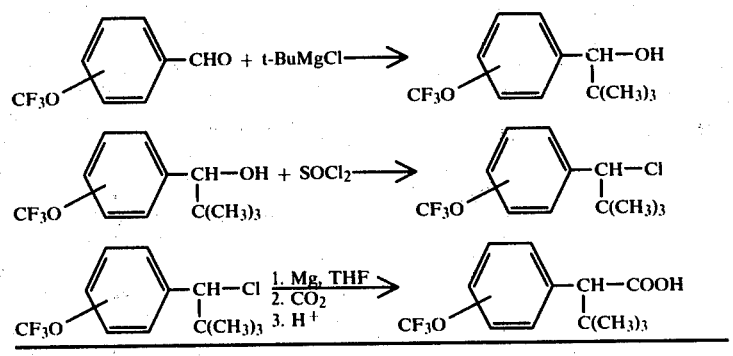

FLOW DIAGRAM V
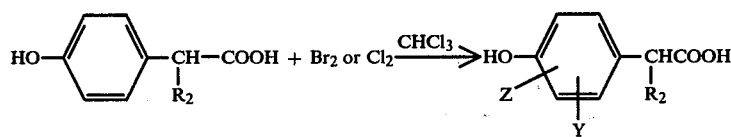
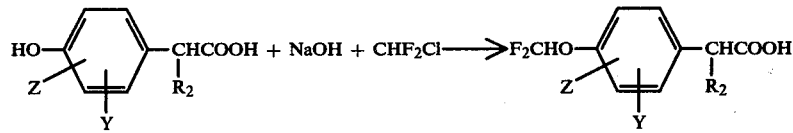
where Z and Y are H, Br and Cl and are meta to the carbon to which the alkanoic acid group is attached.
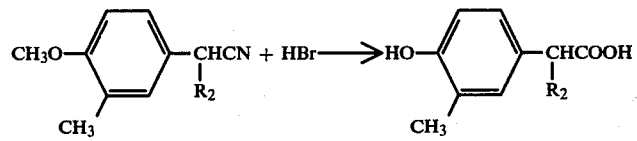
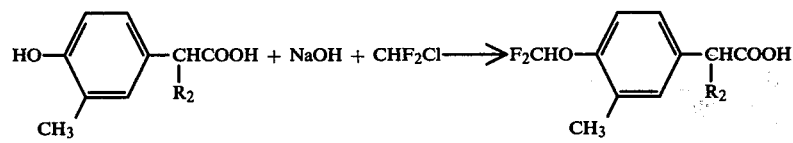
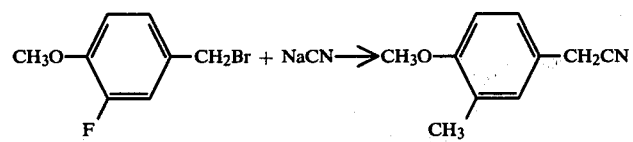
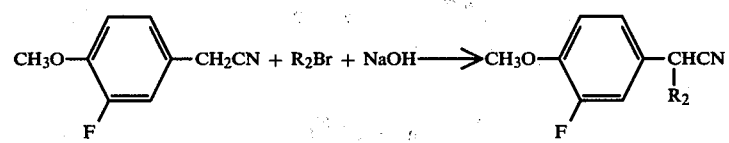
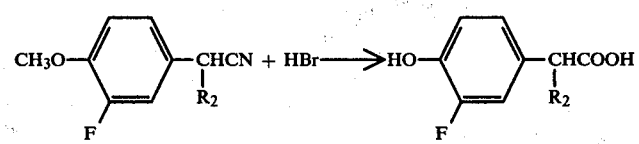
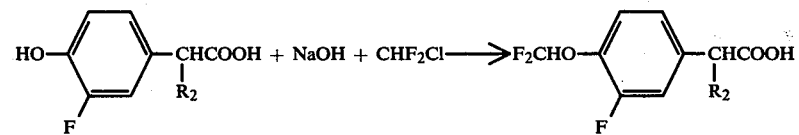
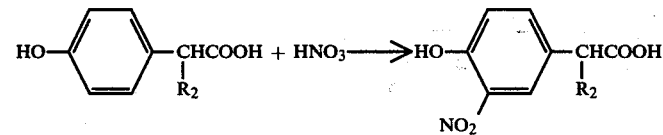
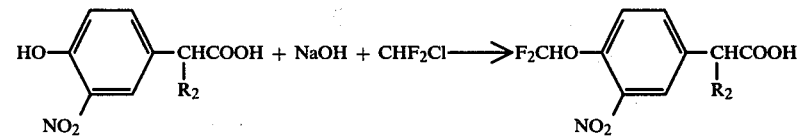
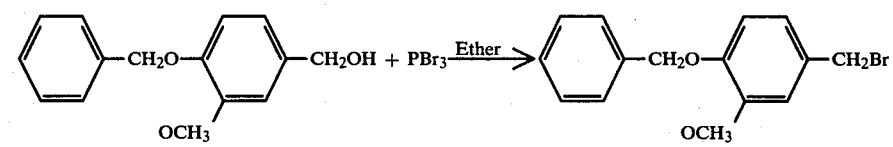

-continued
FLOW DIAGRAM V
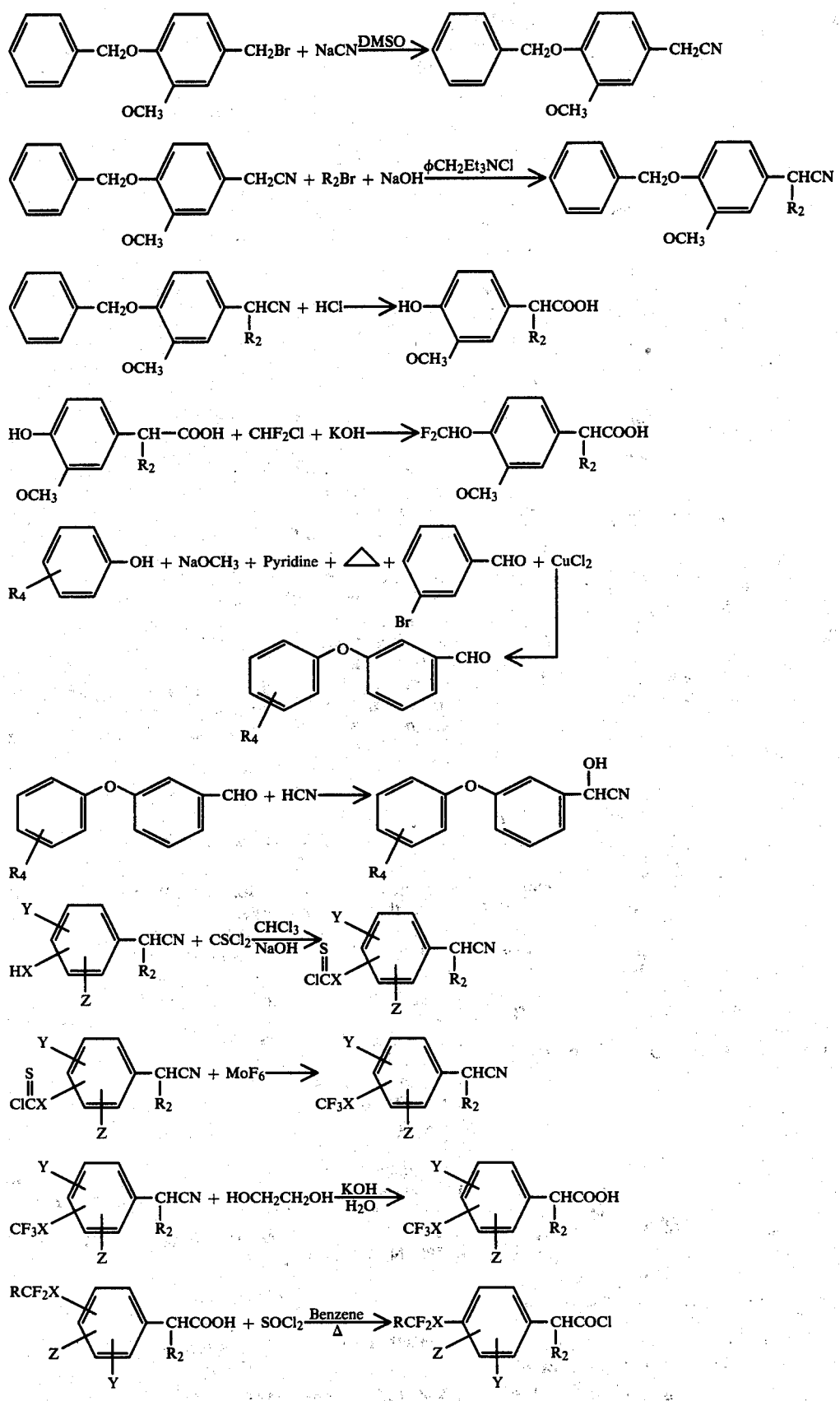

FLOW DIAGRAM V

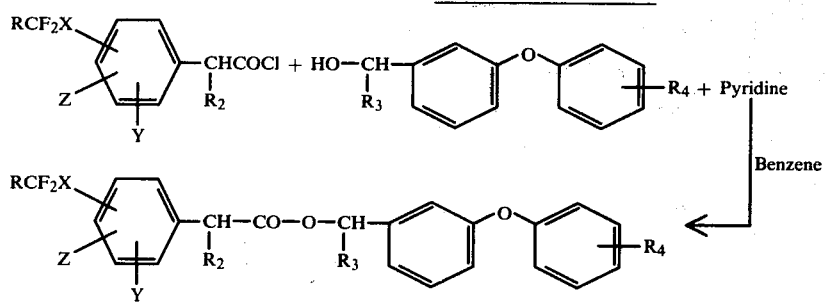

Various optical isomers of the compounds of the invention result from the preparations described herein. For example, it has been found that when α-isopropyl-4-trifluoromethoxyphenylacetic acid is mixed with from about 0.5 to 1.0 molar equivalent of (−)-α-phenethylamine in a suitable solvent such as ethanol or aqueous ethanol, that the salt of the (+)-acid is precipitated. When acidified, this salt releases the acid which is generally in excess of 85% of the (+)-isomer. Higher resolution may be achieved by recrystallization of the (−)-α-phenethylamine salt or by repeating the resolution process with fresh (−)-α-phenethylamine. The m-phenoxybenzyl or α-cyano-m-phenoxybenzyl esters of the completely resolved (+)-α-isopropyl-4-trifluoromethoxyphenylacetic acid are found to be about twice as effective insecticidally as the respective esters prepared from the racemic acid. In the case of the α-cyano-m-phenoxybenzyl ester, an additional increase in activity is obtained when the appropriate optically active α-cyano-m-phenoxybenzyl alcohol is used in the ester-forming step.

EXAMPLE 1

Preparation of p-(1,1,2,2-Tetrafluoroethoxy)toluene

For one hour, tetrafluoroethylene and nitrogen are bubbled into a magnetically stirred mixture of 10.8 g (0.100 mol) of p-cresol, 1.67 g (1.43 g real, 0.0255 mol) of potassium hydroxide pellets, and 70 ml of dried dimethylformamide (DMF) maintained at 68° C. After dilution with 250 ml of water, the reaction mixture is extracted with 100 ml of ether. The ether solution is washed with 200 ml of 5% sodium hydroxide and twice with 400 ml of water. The ether solution is dried, filtered, and then rotary evaporated to give 18.14 g (87%) of p-(1,1,2,2-tetrafluoroethoxy)toluene.

Analysis calculated for $C_9H_8F_4O$: C, 51.93%; H, 3.87%; F, 36.51%. Found: C, 52.06%; H, 3.76%; F, 41.52%.

EXAMPLE 2

Preparation of p-(1,1,2,2-Tetrafluoroethoxy)benzyl bromide

A mechanically stirred mixture of 118.45 g (0.569 mol) of p-(1,1,2,2-tetrafluoroethoxy)toluene, 123.00 g (0.691 mol, 121 mol %) of N-bromosuccinimide (NBS), 1.00 g (4.13 mol, 0.73 mol %) of benzoyl peroxide, and 350 ml of carbon tetrachloride is refluxed for 2.25 hours. After cooling, the reaction mixture is diluted with 350 ml of carbon tetrachloride, filtered to remove the solids, dried with sodium sulfate, filtered, and then evaporated, using a rotary evaporator to give 160.99 g (99%) of a clear red oil. This product is used as is in the subsequent reactions. Infrared and NMR show the product to be p-(1,1,2,2-tetrafluoroethoxy)benzyl bromide.

EXAMPLE 3

Preparation of p-(1,1,2,2-Tetrafluoroethoxy)phenylacetonitrile

Over a period of 40 minutes, a hot solution of 75.1 g (1.15 mol) of potassium cyanide in 140 ml of water is added to a mechanically stirred 75° C. solution of 160.99 g (0.561 mol) of p-(1,1,2,2-tetrafluoroethoxy)benzyl bromide and 500 ml of anhydrous 2B alcohol. The resulting mixture is refluxed for 1.75 hours. After sitting overnight the reaction mixture is poured into 500 ml of cold water and 400 ml of ether. The combined ether solutions are washed twice with 500 ml of water, dried with sodium sulfate, filtered, and then evaporated on a rotary evaporator to give 114.95 g of an oil. A vacuum distillation of this oil gives, as one distillation fraction, 37.10 g (28%) of the nitrile, boiling point 85° C. to 100° C. at 0.29 mm Hg.

EXAMPLE 4

Preparation of α-Isopropyl-p-(1,1,2,2-tetrafluoroethoxy)-phenylacetonitrile

A mixture of 39.85 g (0.171 mol) of p-(1,1,2,2-tetrafluoroethoxy)phenylacetonitrile, 3.71 g (9.96 mmol, 5.8 mol %) of dicyclohexyl-18-crown-6, 22.0 ml (28.8 g, 0.234 mol) of 2-bromopropane, 55 ml of benzene, and 55 ml of 50% sodium hydroxide is stirred for 45 minutes during which there is an exotherm from 25° C. to 43° C. The reaction mixture is then heated at 45° C. for 16.5 hours. After dilution with 200 ml of water, the reaction mixture is extracted with 200 ml of ether. The ether solution is washed with 400 ml of 12% hydrochloric acid, 200 ml of 5% hydrochloric acid, and 300 ml of water. The ether solution is dried with sodium sulfate, filtered, and then evaporated to give 47.13 g of an oil. This oil is vacuum distilled to give 34.83 g (74%), boiling point 83° C. to 85° C. at 0.055 to 0.090 mm Hg.

Analysis calculated for $C_{13}H_{13}F_4NO$: C, 56.73%; H, 4.76%; N, 5.09%; F, 27.61%. Found: C, 56.12%; H, 4.85%; N, 4.99%; F, 34.07%.

EXAMPLE 5

Preparation of 3-Methyl-2-[p-(1,1,2,2-tetrafluoroethoxy)phenyl]-butyric acid

A stirred mixture of 48.0 g (24.0 g real, 0.60 mol) of 50% sodium hydroxide, 21.78 g (0.0791 mol) of α-isopropyl-p-(1,1,2,2-tetrafluoroethoxy)phenylacetonitrile, and 240 ml of ethylene glycol is heated at 135° C. for 12 hours. After dilution with 600 ml of water the reaction mixture is washed twice with 100 ml of ether. The water layer is acidified with concentrated hydrochloric acid and then extracted twice with 300 ml of ether. The ether solution is washed twice with 500 ml of water, dried with sodium sulfate, filtered, and then evaporated to give 20.74 g (89%) of a brown solid, melting point 92° C. to 97° C. (hexane).

Analysis calculated for $C_{13}H_{14}F_4O_3$: C, 53.06%; H, 4,80%; F, 25.83%. Found: C, 53.04%; H, 4,79%; F, 25.93%.

EXAMPLE 6

Preparation of α-Isopropyl-4-methoxyphenylacetonitrile

A solution of sodium hydroxide (50%, 300 ml) is added to a solution of p-methoxyphenylacetonitrile (147 g, 1 mol), dicyclohexyl-18-crown-6 (18.63 g, 5 mol %), 2-bromopropane (320 g, 2.6 mol) and benzene (300 ml). The reaction mixture is heated to 45° C. and held for 4 days. The organic phase is separated, washed well with water (3×200 ml), dilute hydrochloric acid (1×200 ml), water (2×200 ml) and evaporated to an oil. Vacuum distillation gives the product (175.6 g, 81% real): boiling point 96° C. to 100° C. (0.15 mm); nmr (CDCl$_3$) shows that the distilled material contains 12.5 mol % of the starting nitrile.

EXAMPLE 7

Preparation of α-Isopropyl-4-hydroxyphenylacetonitrile

Boron tribromide (51.0 g, 0.2 mol) in methylene chloride (20 ml) is added to a solution of α-isopropyl-4-methoxyphenylacetonitrile (37.8 g, 0.2 mol) in methylene chloride (35 ml) maintained at −40° C. The red solution is allowed to warm to room temperature and stirred for 3 days. The reaction solution is added to ice, then extracted with ether (3×100 ml), washed with water (2×100 ml) and evaporated to an oil. Vacuum distillation gives the product: α-isopropyl-4-hydroxyphenylacetonitrile (28.9 g, 81%); boiling point 142° C. to 143° C. (0.25 mm).

EXAMPLE 8

Preparation of Formic acid, Chlorothio-, O-[p-(1-cyano-2-methylpropyl)phenyl]ester Thiophosgene (16.43 g, 0.143 mol) in chloroform (50 ml) is added over 30 minutes to a solution of α-isopropyl-4-hydroxyphenylacetonitrile (25.0 g, 0.143 mol) in NaOH solution (5%, 5.72 g, 0.143 mol), using an ice bath occasionally to maintain the temperature below 30° C. The mixture is stirred for 15 minutes and the chloroform layer is separated, washed with water and evaporated to a yellow oil (38.2 g). The product is used as such in Example 9.

EXAMPLE 9

Preparation of α-Isopropyl-4-trifluoromethoxyphenylacetonitrile

The thiocarbonate (38.2 g) from Example 8 is treated with molybdenum hexafluoride (15.8 g) at −25° C. The thick reaction mass is then allowed to warm to room temperature and then heated slowly to 160° C. using an oil bath. The mixture is cooled to room temperature and then poured into water and extracted with ether (4×50 ml), washed with water (1×50 ml) and evaporated to an oil. Vacuum distillation gives α-isopropyl-4-trifluoromethoxyphenylacetonitrile; boiling point 78° C. to 80° C. (0.15 mm).

EXAMPLE 10

Alternate Preparation of α-Isopropyl-4-trifluoromethoxyphenylacetonitrile

A. Preparation of 4-Trifluoromethoxybenzyl chloride

A mixture of trioxane (355 mg), zinc chloride (340 mg) and trifluoromethoxybenzene (600 mg) is heated at 73° C. while hydrogen chloride gas is bubbled through the reaction mixture. The reaction is cooled to room temperature and diluted with ether. The organic phase is washed with saturated sodium carbonate solution and water. Removal of the solvents gives the product as a colorless liquid (1.42 g).

B. Preparation of 4-Trifluoromethoxyphenylacetonitrile

The above chloro compound is converted to the corresponding nitrile by the procedure used in Example 3 in 93% yield.

C. Preparation of α-Isopropyl-4-trifluoromethoxyphenylacetonitrile

The alkylation of 4-trifluoromethoxyphenylacetonitrile is carried out in 90% yield by the procedure illustrated in Example 4.

EXAMPLE 11

Preparation of α-isopropyl-4-(trifluoromethoxy)phenylacetic acid

A mixture of α-isopropyl-4-trifluoromethoxyphenylacetonitrile (2.0 g), potassium hydroxide (3.0 g) in ethylene glycol (35 ml) and water (3 ml) is heated at 140° C. for 8 hours. The solution is poured into water and extracted with ether (2×10 ml). The aqueous layer is acidified with dilute hydrochloric acid and extracted with ether (3×11 ml), washed with water (1×25 ml), dried (Na$_2$SO$_4$) and evaporated to an oil (1.23 g); IR (neat) 1700 cm$^{-1}$.

The 2-haloalkyl(oxy-, thio-, sulfinyl-, or sulfonyl) phenylalkanoic acids are useful in preparing insecticidal m-phenoxybenzyl ester of 2-(haloalkoxyphenyl)alkanoic acids as shown in Flow Diagram I.

EXAMPLE 12

Preparation of α-isopropyl-4-(trifluoromethoxy)phenylacetyl chloride

A solution of α-isopropyl-4-trifluoromethoxyphenylacetic acid (1.2 g) and thionyl chloride (0.6 ml) in benzene (5 ml) is refluxed for 4 hours. Evaporation of the solvent and excess thionyl chloride gives the acid chloride which is used as such for esterification in Example 13.

EXAMPLE 13

Preparation of α-cyano-m-phenoxybenzyl α-isopropyl-4-(trifluoromethoxy)phenylacetate A solution of α-isopropyl-4-trifluoromethoxyphenylacetyl chloride (4.58 mmole) in ether (5 ml) is added to a ether (20 ml) solution of α-cyano-m-phenoxybenzyl alcohol (4.58 mmole) and pyridine (0.5 ml). The mixture is stirred overnight and filtered. The filtrate and the washings are evaporated and the residual oil is purified on 5×2 mm silica gel plates using 1:1 methylenechloride-hexane as eluent. The band with Rf=0.55 is extracted with ether and evaporated to give the desired ester (0.85 g).

IR (neat) 1755 cm$^{-1}$; NMR (CDCl$_3$ δ 6.8–7.6 (m, 13H, ArH̲), 6.31 and 6.28 (S, 1H,

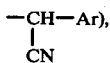

3.27 (d, J=7 Hz, 1H, CH̲—CH(CH$_3$)$_2$), 2.0–2.6 (m, 1H, CH̲(CH$_3$)$_2$), 0.6–1.2 (four doublets, J=7 Hz, 6H, isopropyl CH$_3$); 19F chemical shift 58.8 δ relative to CFCl$_3$.

EXAMPLE 14

Preparation of m-Phenoxybenzyl α-isopropyl-4-trifluoromethoxyphenylacetate

To a solution of m-phenoxybenzyl alcohol (1.89 g) and pyridine (1 ml) in methylene chloride (6 ml) is added a methylene chloride (7 ml) solution of α-isopropyl-4-trifluoromethoxyphenylacetyl chloride, prepared from the corresponding acid (2.46 g) as illustrated in Example 15. After stirring the reaction mixture overnight, it is washed with water, diluted hydrochloric acid solution, dilute potassium hydroxide solution, water and evaporated to an orange oil. Purification by silica gel chromatography gives the desired ester (2.76 g).

IR (neat) 1738 cm$^{-1}$; nmr (CDCl$_3$) δ 6.73–7.45 (m, 13H), 5.03 (S, 2H), 3.20 (d, J=10.5 Hz, 1H), 2.26 (m, 1H), 0.66 and 0.94 (two d, J=6.6 Hz, 6H).

EXAMPLE 15

Preparation of α-Ethyl- and α-n-propyl-4-trifluoromethoxyphenylacetic acids and esters thereof Following the procedure of Example 6, but substituting ethyl bromide and 1-bromopropane for 2-bromopropane and proceeding with the steps exemplified by Examples 7, 8, 9 and 11, afforded the acids, α-ethyl-4-trifluoromethoxyphenylacetic and α-n-propyl-4-trifluoromethoxyphenylacetic acids, respectively.

EXAMPLE 16

Preparation of α-Bromo-4-trifluoromethylthiotoluene

Bromine (20.5 g, 0.13 mol) in 20 ml of carbon tetrachloride is added slowly to a solution of 4-trifluoromethylthiotoluene (29 g, 0.15 mol) in 90 ml of carbon tetrachloride heated to gentle reflux under a 275 W sunlamp. When the addition is complete, the solution is maintained at reflux for one hour. Most of the solvent is removed at atmospheric pressure, then the residue is vacuum distilled. The 15.5 g cut with boiling point 64°–77° C./0.6–0.8 mm is 92% monobromo compound by glc.

EXAMPLE 17

Preparation of 4-Trifluoromethylthiophenylacetonitrile

Sodium cyanide (3.9 g, 0.08 mol) is added to 40 ml of dimethylsulfoxide at 65° C. under N$_2$. The heat is removed and α-bromo-4-trifluoromethylthiotoluene (14.3 g real, 0.053 mol) is added dropwise at such a rate that the exotherm never raises the temperature above 75° C. The red-colored reaction is heated to 90°–95° C. for about 45 minutes, then cooled to room temperature and treated with 50–100 ml of ice water. The aqueous suspension is extracted with several portions of ether which are combined, washed with water, and dried over sodium sulfate. Evaporation in vacuo gives 9.7 g of a dark red oil 95% pure by glc.

EXAMPLE 18

Preparation of α-Isopropyl-4-trifluoromethylthiophenylacetonitrile

Fifty percent sodium hydroxide (13.5 ml) is added over a 30-minute period dropwise to a suspension of 4-trifluoromethylthiophenylacetonitrile (9.7 g, 0.045 mol), 2-iodopropane (9.5 g, 0.056 mol), and 18 crown-6 (0.61 g, 0.0023 mol) in 13.5 ml of benzene and the exotherm reaches 43° C. After stirring 2.5 hours at ambient temperature, an aliquot placed on glc shows none of the starting nitrile remaining. The reaction is worked up by adding ice water and extracting with ether, which is washed with 10% HCl, water, and dried over sodium sulfate. Evaporation in vacuo gave 10.2 g (86.8%) of a red-brown oil.

Comparable results are obtained substituting ethyl bromide or n-propyliodide in place of 2-iodopropane to synthesize α-ethyl-4-trifluoromethylthiophenylacetonitrile and α-n-propyl-4-trifluoromethylthiophenylacetonitrile, respectively.

EXAMPLE 19

Preparation of α-Isopropyl-4-trifluoromethylthiophenylacetic acid

α-Isopropyl-4-trifluoromethylthiophenylacetonitrile (6.9 g real, 0.0265 mol) and 50% sodium hydroxide (25 g, 0.312 mol) are combined in 53 ml of ethylene glycol and heated at gentle reflux for 18 hours. The reaction is poured into ice water and extracted with ether. The aqueous phase is acidified with concentrated HCl, then re-extracted with ether which is washed with water and dried over sodium sulfate. Evaporation in vacuo gives 2.05 g of an oil product.

Comparable results are obtained substituting α-ethyl-4-trifluoromethylthiophenylacetonitrile or α-n-propyl-4-trifluoromethylthiophenylacetonitrile, as the starting material to synthesize α-ethyl-4-trifluoromethylthiophenylacetic acid and α-n-propyl-4-trifluoromethylthiophenylacetic acid, respectively.

EXAMPLE 20

Preparation of α-Isopropyl-4-mercaptophenylacetic acid

A solution of α-isopropyl-4-difluoromethylthiophenylacetonitrile (15.7 g, 0.065 mol) in sodium hydroxide solution (50%, 42 g) and ethylene glycol (80 ml) is heated at reflux for 18 hours. The reaction mixture is poured into ice water and extracted with ether. The alkaline layer is acidified at 15°–20 ° C. using concentrated hydrochloric acid and extracted with ether. The ether extract is washed with water, saturated sodium chloride solution and evaporated to give an oil (11.4 g, 83%). NMR and ir indicate that the —CHF$_2$ radical has been removed during the reaction and the product is the thiol.

EXAMPLE 21

Preparation of
α-Isopropyl-4-difluoromethylthiophenylacetic acid

Sodium hydroxide (18.4 g, 0.46 mol) in 50 ml of water and α-isopropyl-4-mercaptophenylacetic acid (11 g, 0.05 mol) in 40 ml of dioxane are combined and heated to a temperature of 50° C. Chlorodifluoromethane (Freon-22) is bubbled in slowly under the surface of the liquid causing an immediate exotherm to 75° C. The addition is continued until the exotherm slowly begins to subside (about 0.5 hour). The reaction is cooled to room temperature and treated with 100 ml of ice water. The aqueous layer is extracted with 3×200 ml of ether, then acidified at 15°-20° C. with concentrated HCl. The resulting oil is removed by ether extraction. The ether solution is washed with water and saturated sodium chloride before drying over sodium sulfate and evaporation in vacuo to give 10.2 g of a dark brown gum. This is used without further purification in the final esterification step.

EXAMPLE 22

Preparation of α-Isopropyl-4-hydroxyphenylacetic acid

A mixture of α-isopropyl-4-methoxyphenylacetonitrile (40.0 g) and hydrobromic acid (48%, 200 ml) is refluxed at 126°-128° C. using an oil bath for 14 hours. The reaction mixture is diluted with ice and water, extracted several times with ether, washed with water and evaporated to a solid residue. The solid is boiled with cloroform (200 ml), cooled, filtered and dried: yield, 23.8 g; melting point 172°-174° C.; ir (Nujol) 3250-2900 (broad, OH), 1690 cm$^{-1}$ (C=O).

Comparable results are obtained substituting α-ethyl-4-methoxyphenylacetonitrile or α-n-propyl-4-methoxyphenylacetonitrile to synthesize α-ethyl-4-hydroxyphenylacetic acid and α-n-propyl-4-hydroxyphenylacetic acid, respectively.

EXAMPLE 23

Preparation of
α-Isopropyl-4-difluoromethoxyphenylacetic acid

Into an 80° C. magnetically stirred mixture of 10.00 g (0.0515 mol) of α-isopropyl-4-hydroxyphenylacetic acid, 65 ml of dioxane, 19.08 g (18.56 g real, 0.464 mol) of sodium hydroxide, and 30 ml of water is bubbled 46 g (0.532 mol) of chlorodifluoromethane over a period of 4 hours. The reaction mixture is poured into 250 ml of ice water and the resulting mixture is washed with ether, acidified with concentrated hydrochloric acid to pH 3, and then extracted with 200 ml of ether. The ether solution is washed once with 100 ml of water, dried with sodium sulfate, filtered, and then evaporated to give a white paste. A mixture of hexane and methylene chloride is added and the resulting mixture is filtered to remove the solid which is the starting material. The filtrate is evaporated to give 5.41 g of a clear brown oil. It is estimated that the product was at least 85% pure by nmr. NMR (CDCl$_3$-d$_5$ pyridine), δ 7.43 (d, J=8.2 Hz, 2H), δ 7.08 (d, J=8.2 Hz, 2H), δ 6.57 (t, J=74.3 Hz, 1H), δ 3.63 (s, imp.), δ 3.25 (d, J=10 Hz, 1H), δ 2.37 (m, 1H), δ 1.19 (d, J=6.5 Hz, 3H), δ 0.78 (d, J=6.5 Hz, 3H), δ 13.82 (s, 1H).

Comparable results are obtained substituting α-ethyl-4-hydroxyphenylacetic acid or α-n-propyl-4-hydroxyphenylacetic acid to synthesize α-ethyl-4-difluoromethoxyphenylacetic acid and α-n-propyl-4-difluoromethoxyphenylacetic acid, respectively.

EXAMPLE 24

Preparation of 4-Trifluoromethoxy-α-t-butylbenzyl alcohol

To a solution of commercially available t-butyl magnesium chloride in THF (1.0 mol) is added at 38°-40° C. a solution of 4-trifluoromethoxybenzaldehyde (56 g, 0.4 mol) in THF (50 ml) under nitrogen atmosphere. The reaction solution is stirred at room temperature overnight and cautiously acidified with dilute sulfuric acid at 15°-20° C. Ether is added and the organic phase is washed with water, dried (Na$_2$SO$_4$) and evaporated to a gummy solid. The crude material is purified by silica gel chromatography to give the alcohol which is used in Example 25.

EXAMPLE 25

Preparation of
p-(1-Chloro-2,2-dimethylpropyl)-α,α,α-trifluoroanisole

To freshly distilled thionyl chloride (14.87 g, 0.125 mol) cooled in salt ice bath is added in portions the neopentyl alcohol of Example 24 (12.4 g, 0.05 mol) over 30 minutes. The ice bath is removed and the slurry is left to stand overnight. Evaporation of excess thionyl chloride gives a solid.

EXAMPLE 26

Preparation of
α-t-Butyl-4-trifluoromethoxyphenylacetic acid

The neopentyl chloride prepared in Example 25 is converted to the Grignard reagent and subsequent carbonation with carbon dioxide according to the procedure of Weinstein and Morse [*Journal of the American Chemical Society* 74, 1133 (1952)] gives the desired acid as a white solid.

EXAMPLE 27

Preparation of
α-Isopropyl-3-bromo-4-hydroxyphenylacetic acid

A mixture of α-isopropyl-4-hydroxyphenylacetic acid (20 g, 0.103 mol) in chloroform (250 ml) is cooled to 0° C. and bromine (16.5 g, 0.103 mol) in chloroform (15 ml) is added over 30 minutes. The reaction solution is stirred at 0° C. for 30 minutes and then allowed to warm to room temperature. The solvent is evaporated and the residue is crystallized from hexanes-benzene to give the monobromo derivative (22.1 g); melting point 113° C. to 116° C.

EXAMPLE 28

Preparation of
α-Isopropyl-3-bromo-4-difluoromethoxyphenylacetic acid

Using the procedure described in Example 23, α-isopropyl-3-bromo-4-hydroxyphenylacetic acid (18.0 g) is converted to the corresponding difluoromethoxy acid. The desired acid is obtained by separation of the unreacted starting material by chromatography on silica gel using 2.5% methanol in chloroform as eluent as a waxy solid (4.7 g). This crude acid is used as such in Example 29 and 30.

EXAMPLE 29

Preparation of m-Phenoxybenzyl α-isopropyl-3-bromo-4-difluoromethoxyphenylacetate By using α-isopropyl-3-bromo-4-difluoromethoxyphenylacetic acid and procedures of Examples 12 and 14, the product is obtained as a pale yellow gum. NMR (CDCl$_3$), δ 6.8–7.7 (m, 12H, ArH), 6.45 (t, J=74 Hz, 1H, OCHF$_2$), 5.10 (bs, 1H, CH$_2$) 3.18 (d, J=9 Hz, 1H, CH—CH(CH$_3$)$_2$), 1.0 and 0.71 (2d, J=6 Hz, isopropyl CH$_3$).

EXAMPLE 30

Preparation of α-Cyano-m-phenoxybenzyl α-isopropyl-3-bromo-4-difluoromethoxyphenylacetate By using α-isopropyl-3-bromo-4-difluoromethoxyphenylacetic acid and procedures of Examples 11 and 13, the product is obtained as a yellow gum. NMR (CDCl$_3$) δ 6.9–7.7 (m, 12H, ARH), 6.50 (t, J=74 Hz, 1H, OCHF$_2$) 6.33 and 6.36 (2S, 1H, CH—CN), 3.25 (d, 1H, CH—CH(CH$_3$), 0.6–1.1 (4d, 6H, isopropyl CH$_3$).

EXAMPLE 31

Preparation of α-Isopropyl-3-chloro-4-hydroxyphenylacetic acid

A mixture of α-isopropyl-4-hydroxyphenylacetic acid (30 g., 0.154 mol) in chloroform (600 ml) is cooled to 0° to 5° C. and chlorine gas (12.0 g., 0.169 mol) is bubbled slowly. The solvent is removed and the product is obtained by crystallization from benzene-hexanes: m.p. 125°–128° C.

EXAMPLE 32

Preparation of α-cyano-m-phenoxybenzyl α-isopropyl-3-chloro-4-difluoromethoxyphenylacetate By using α-isopropyl-3-chloro-4-hydroxyphenylacetic acid and procedures of Examples 23, 12, and 13, the product is obtained as a gum. NMR (CDCl$_3$) δ 6.8 to 7.5 (m, 12H, ArH), 6.50 (t, J=74 Hz, 1H, OCHF$_2$), 6.33 and 6.30 (2S, 1H, —CH—CN), 3.25 (d, J=10 Hz, 1H, CH—CH(CH$_3$)$_2$).

Analysis calculated for C$_{26}$H$_{22}$ClF$_2$NO$_4$: C 64.26; H 4.56; N 2.88; Cl 7.30; F 7.82. Found: C 64.27; H 4.70; N 2.94; Cl 7.20; F 7.78.

EXAMPLE 33

Preparation of m-Phenoxybenzyl α-isopropyl-3-chloro-4-difluoromethoxyphenylacetate By using α-isopropyl-3-chloro-4-hydroxyphenylacetic acid and procedures of Examples 25, 12 and 14, the product is obtained as a yellow oil. NMR (CDCl$_2$) δ 6.8 to 7.6 (m, 12H, ArH), 6.47 (t, J=74 Hz, OCHF$_2$), 5.07 (bs, 2H, CH$_2$).

Analysis calculated for C$_{25}$H$_{23}$ClF$_2$O$_4$: C 65.15; H, 5.03; Cl 7.69; F 8.24. Found: C 65.46; H 5.05; Cl 7.73; F 8.08.

EXAMPLE 34

Preparation of α-Isopropyl-3,5-dichloro-4-hydroxyphenylacetic acid

A mixture of α-isopropyl-4-hydroxyphenylacetic acid (30 g, 0.155 mol) is chloroform (500 ml) is chilled in ice-salt bath and chlorine gas (ca 30–35 g) is bubbled at 0° to 5° C. for 90 minutes. The solution is stirred at 0° to 5° C. for an additional hour and allowed to warm to room temperature. The solvent is evaporated and the product is obtained by crystallization from hexanes as a white solid (29.8 g); m.p. 152°–154°.

EXAMPLE 35

Preparation of α-Isopropyl-3,5-dichloro-4-difluoromethoxyphenylacetic acid

By using α-isopropyl-3,5-dichloro-4-hydroxyphenylacetic acid and procedure of Example 23, the above acid is obtained as an oil. The nmr of the product indicates that it contains 15 mole percent (approx.) of the starting material, and is used as such in Example 36.

EXAMPLE 36

Preparation of α-Cyano-m-phenoxybenzyl α-isopropyl-3-bromo-4-difluoromethoxyphenylacetate By using α-isopropyl-3,5-dichloro-4-difluoromethoxyphenylacetic acid and procedures of Examples 12 and 13, the product is obtained as a yellow gum, NMR (CDCl$_3$) δ 6.9–7.7 (m, 11GH, ArH), 6.67 (t, J=74 Hz, 1H, OCHF$_2$), 6.33 and 6.40 (2S, 1H, CH—CN), 3.23 (d, J=10Hz, 1H, CH—CH(CH$_3$)$_2$, 0.6 to 1.1 (4d, 6H, isopropyl CH$_3$).

Analysis calculated for C$_{22}$H$_2$Cl$_2$F$_2$NO$_4$: C 60.01; H 4.07; N 2.69. Found: C 59.78; H 4.30; N 2.31.

EXAMPLE 37

Preparation of m-Phenoxybenzyl α-isopropyl-3,5-dichloro-4-difluoromethoxyphenylacetate By using α-isopropyl-3,5-dichloro-4-difluoromethoxyphenylacetic acid and procedures of Examples 12 and 14, the product is obtained as a gum.

Analysis calculated for C$_{25}$H$_{22}$Cl$_2$F$_2$O$_4$: C 60.61; H 4.48; Cl 14.32; F 7.67. Found: C 60.50; H 4.60; Cl, 14.13; F 7.52.

EXAMPLE 38

Preparation of α-Isopropyl-3-methyl-4-difluoromethoxyphenylacetic acid

3-Methyl-4-methoxyphenylacetonitrile is converted to the above compound using procedures of Examples 6, 22, and 23. The product is contaminated with some α-isopropyl-3-methyl-4-hydroxyphenylacetic acid as indicated by nmr. However, the material is used as such for esterification in Example 39 where the final ester is purified by chromatography.

EXAMPLE 39

Preparation of α-cyano-m-phenoxybenzyl α-isopropyl-3-methyl-4-difluoromethoxyphenylacetate Using the acid obtained in Example 38 and the procedures of Examples 12 and 13, the ester is obtained as a viscous oil. NMR (CDCl$_3$) δ 6.8–7.6 (m, 12H, ArH), 6.45 (t, J=74 Hz, 1H, OCHF$_2$), 6.48 and 6.53 (2S, 1H, CH—CN), 2.25 (S, 3H, CH$_3$).

Analysis calculated for C$_{27}$H$_{25}$F$_2$NO$_4$: C 69.66; H 5.41; N 3.01. Found: C 70.05; H 5.86; N 2.83.

EXAMPLE 40

Preparation of 3-Fluoro-4-methoxyphenylacetonitrile

A mixture of 4-(bromomethyl)-2-fluoroanisole (45.8 g, 0.21 mol), trihexylamine (1.4 g) and sodium cyanide (20.5 g, 0.42 mol) in water (50 ml) is heated at 60°–65° C.

for 18 hours. The mixture is cooled and extracted in its ether, washed with water, saturated sodium chloride solution and dried (CNa₂SO₄). Evaporation of the solvent gives a solid, (33.2 g); m.p. 42°–46° C.

EXAMPLE 41

Preparation of α-Isopropyl-3-fluoro-4-methoxyphenylacetonitrile

A mixture of 3-fluoro-4-methoxyphenylacetonitrile (30 g, 0.18 mol), 2-bromopropane (27.7 g, 0.225 mol), benzyltriethylammonium chloride (2.3 g, 0.01 mol) and sodium hydroxide solution (50%, 66 ml) is heated at 55° for 1 hour and cooled. The mixture is diluted with water, extracted with ether, washed with water, 1 NHCl, water, and dried (Na₂SO₄). Evaporation gives the product as a brown oil (30.7 g). NMR spectrum shows the benzylic proton as a doublet at 3.6 δ.

EXAMPLE 42

Preparation of α-Isopropyl-3-fluoro-4-difluoromethoxyphenylacetic acid

Starting with α-isopropyl-3-fluoro-4-methoxyphenylacetonitrile and following the procedures of Examples 22 and 23, the product is obtained as a brown oil. NMR spectrum shows that the product is contaminated with the starting material. Hence this crude reaction mixture is subjected to the Freon 22 reaction two more times as described in Example 23 to give the product as a brown oil. NMR spectrum indicates that the product is approximately 96% by weight.

EXAMPLE 43

Preparation of α-cyano-m-phenoxybenzyl α-isopropyl-3-fluoro-4-difluoromethoxyphenylacetate Starting with α-isopropyl-3-fluoro-4-difluoromethoxyphenylacetic acid and following the procedures of Examples 12 and 13, the final ester is prepared as yellow oil. NMR (CDCl₃) δ 6.8 to 7.5 (m, 12H, ArH), 6.63 (t, J=74 Hz, 1H, OCHF₂), 6.33 and 6.37 (2S, 1H, CH—CN).

Analysis calculated for $C_{26}H_{22}F_3NO_4$: C 66.52; H 4.72; N 2.98. Found: C 66.27; H 4.87; N 2.99.

EXAMPLE 44

Preparation of α-Isopropyl-3-nitro-4-hydroxyphenylacetic acid

A mixture of α-isopropyl-4-hydroxyphenylacetic acid (18.2 g, 0.094 mol) in acetic acid (130 ml) is heated to 40° C. and nitric acid (70%, 9.56 g, 0.095 mol) is added at such a rate that the reaction temperature is maintained at 38°–40° and never exceeded 45° C. The reaction mixture is stirred at 40°–42° C. overnight and poured into ice-water. The yellow solid is collected by filtration, washed and dried (19.1 g); m.p. 103°–105°.

EXAMPLE 45

Preparation of α-Isopropyl-3-nitro-4-difluoromethoxyphenylacetic acid

Using α-isopropyl-3-nitro-4-hydroxyphenylacetic acid and procedure of Example 23, the above acid is prepared as a crude material containing unreacted starting material. However, repeating of the Freon 22 reaction as described in Example 23 three times using the crude product obtained after each cycle, the product is finally obtained as a fine beige solid (hexanes): m.p. 88°–90°.

EXAMPLE 46

Preparation of α-Cyano-m-phenoxybenzyl α-isopropyl-3-nitro-4-difluoromethoxyphenylacetate Using α-isopropyl-3-nitro-4-difluoromethoxyphenylacetic acid and procedures of Examples 12 and 13, the product is obtained as a yellow oil.

Analysis calculated for $C_{26}H_{22}F_2N_2O_6$: C 62.90; H 4.47; N 5.64. Found: C 62.51; H 4.77; N 5.58.

EXAMPLE 47

Preparation of α-Cyano-m-phenoxybenzyl α-isopropyl-3-methoxy-4-difluoromethoxyphenylacetate Using α-isopropyl-3-methoxy-4-difluoromethoxyphenylacetic acid and procedures of Examples 12 and 13, the product can be prepared as a gum.

EXAMPLE 48

Preparation of m-(m-Fluorophenoxy)benzaldehyde

The sodium salt of 3-fluorophenol is prepared by mixing 3-fluorophenol (15.13 g, 0.135 mol) and sodium methoxide (7.29 g, 0.135 mol) in pyridine (115 ml). The reaction is heated to 110° C. during which 34 ml of pyridine-methanol is distilled off. The reaction is cooled to 80° C. and m-bromobenzaldehyde (25.0 g, 0.135 mol) and copper (I) chloride (4.05 g, 0.049 mol) are added. The reaction mixture is refluxed overnight. The following day, most of the pyridine is removed by distillation and the reaction is cooled and diluted into toluene (80 ml). The solids are filtered and the filtrate is washed with 20% HCl, water, 5% NaOH, and water, respectively and evaporated to a dark brown oil. Vacuum Distillation gives the product as a clear liquid (6.6 g): b.p. 82°–88° C. (0.5 mm).

Analysis calculated for $C_{13}H_9FO_2$: C 72.22; H 4.20; F 8.79. Found: C 72.03; H 4.30; F 8.60.

EXAMPLE 49

Preparation of substituted α-Cyano-m-phenoxybenzyl esters of fluoroalkoxyphenylacetic acids Starting with either α-isopropyl-4-difluoromethoxyphenylacetic acid or α-isopropyl-4-trifluoromethoxyphenylacetic acid and the cyanohydrin of an appropriately substituted aldehyde, and using procedures of Examples 12 and 13, the following esters are prepared:

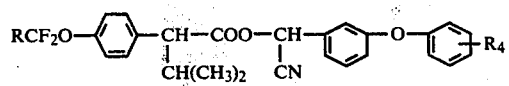

| R | R₄ | NMR Assignments | Analysis Calculated | Analysis found |
|---|----|----|----|----|
| | | δ 6.8 to 7.5 (m, 12H, ArH), 6.45 (t, J=74Hz, 1H, OCHF₂), | C 64.27<br>H 4.56 | C 64.54<br>H 4.92 |

-continued

| R | R$_4$ | NMR Assignments | Analysis Calculated | Analysis found |
|---|---|---|---|---|
| H | p-Cl | 6.30, 6.33 (2S, 1H, CH—CN), 3.25 (d, J=10Hz, 1H, CH—CH(CH$_3$)$_2$), 0.6 to 1.2 (d, 6H, isopropyl CH$_3$) 6.8 to 7.4 (m, 12H, ArH) 6.47 (t, J=74Hz, 1H, OCHF$_2$), | N 2.88 C 67.35 H 5.23 | N 2.82 C 67.30 H 5.46 |
| H | p-OCH$_3$ | 6.28, 6.33 (2S, 1H, CN—CN), 3.80 (S, 3H, OCH$_3$) 6.8 to 7.5 (m, 12H, ArH), 6.50 (t, J=74Hz, 1H, OCHF$_2$), | N 2.91 C 69.67 H 5.41 | N 2.92 C 69.37 H 5.72 |
| H | p-CH$_3$ | 6.33, 6.37 (2S, 1H, CH—CN), 2.40 (S, 3H, CH$_3$) 6.8 to 7.5 (m, 12H, ArH), 6.47 (t, J=74Hz, 1H, OCHF$_2$), | N 3.01 C 66.51 H 4.73 | N 2.82 C 66.48 H 4.95 |
| H | p-F | 6.30, 6.36 (2S, 1H, —CH—CN), 6.8 to 7.5 (m, 12H, ArH) 6.32, 6.37 (2S, 1H, —CH—CN), 3.30 (d, J=10Hz, 1H, CH—CH(CH$_3$)$_2$) | N 2.98 C 64.06 H 4.35 | N 2.64 C 63.85 H 4.31 |
| F | p-F | 6.8 to 7.4 (m, 12H, ArH), 6.43 (t, J=74Hz, 1H, OCHF$_2$), 6.30 and 6.34 (2S, 1H, —CH—CN), 3.27 (d, J=10Hz, 1H, CH—CH(CH$_3$)$_2$) | N 2.87 C 66.52 H 4.72 N 2.98 F 12.14 | N 2.63 C 66.68 H 4.80 N 3.04 F 12.05 |
| H | o-F | 6.5 to 7.5 (m, 12H, ArH), 6.33 and 6.39 (2S, 1H, —CH—CN), 6.47 (t, J=74Hz, 1H, OCHF$_2$), 3.28 (d, J=10Hz, 1H, CH—CH(CH$_3$)$_2$) | C 66.52 H 4.72 N 2.98 F 12.14 | C 66.80 H 4.77 N 2.89 F 11.93 |
| H | m-F | 6.8 to 7.5 (m, 12H, ArH), 6.37 and 6.41 (2S, 1H, —CH—CN), 3.33 (d, J=10Hz, CH—CH(CH$_3$)$_2$), 0.6 to 1.2 (4d, 6H, isopropyl CH$_3$) | C 61.97 H 4.20 N 2.78 | C 62.05 H 4.25 N 2.52 |
| F | p-Cl | 6.8 to 7.4 (m, 12H, ArH), 6.37 and 6.41 (2S, 1H, —CH—CN) 2.40 (S, 3H, CH$_3$) | C 67.07 H 5.00 N 2.90 | C 65.28 H 5.18 N 2.26 |
| F | p-CH$_3$ | 6.9 to 7.5 (m, 12H, ArH), 6.25 and 6.30 (2S, 1H, CH—CN), 3.63 (S, 3H, OCH$_3$) | C 64.92 H 4.84 N 2.80 | C 64.04 H 4.87 N 2.65 |
| F | p-OCH$_3$ | | | |

EXAMPLE 50

Resolution of α-Isopropyl-4-difluoromethoxyphenylacetic Acid

A warm solution (60° C.) of (—)-2-phenylamine (4.96 g) in aqueous ethanol (60% ethanol, 20 ml) is added to a warm solution (60° C.) of the racemic acid (20 g) in aqueous ethanol (60% ethanol, 50 ml) with magnetic stirring. As the solution is allowed to cool slowly to room temperature, the salt precipitates out as white crystalline solid. The mixture is allowed to stand overnight and the solids are collected by filtration, washed with aqueous ethanol (10 ml) and dried (9.5 g): m.p. 184°–188°. The resolved acid obtained from the above salt is found to have a rotation $[\alpha]_D^{R.T.} = +37.1°$ (CHCl$_3$, C=1.439 g/100 ml). Two more crystallizations of the above salt from aqueous ethanol (60% ethanol) gives white needles, m.p. 185°–187° C., from which the resolved acid is obtained with $[\alpha]_D^{R.T.} = +40.4°$ (CHCl$_3$, C=1.353 g/100 ml).

EXAMPLE 51

Preparation of (±)-α-Cyano-m-phenoxybenzyl (±)-α-isopropyl-4-difluoromethoxyphenylacetate The resolved (±)-acid obtained in the above example is converted to the ester using the procedures of Examples 12 and 13. $N_D^{23}=1.5432$; NMR (CDCl$_3$) δ 6.8 to 7.5 (m, 13H, ArH), 6.43 (t, J=74 Hz, OCHF$_2$), 6.30 and 6.23 (2S, 1H, CH—CN), 3.27 (d, J=10Jz, 1H, CH—CH(CH$_3$)$_2$).

EXAMPLE 52

Resolution of α-Isopropyl-4-trifluoromethoxyphenylacetic acid

A mixture of the racemic acid (26.2 g) and (—)-α-phenethylamine (12.1 g) in aqueous ethanol (60% ethanol, 2 l) is heated to dissolution on a steam bath and allowed to cool slowly to room temperature. The salt is collected by filtration and dried (16.9 g): m.p. 189°–193°. The salt is crystallized twice from aqueous ethanol (60% ethanol, 1 l and 600 ml respectively): m.p. 194°–196° (8.0 g). The (+)-acid is obtained by neutralization of the salt with dilute hydrochloric acid and extraction with ether and evaporation of the solvent: $[\alpha]_D^{R.T.} = +35.5°$ (CHCl$_3$, C=6.0 g/100 ml).

EXAMPLE 53

Preparation of (±)-α-Cyano-m-phenoxybenzyl (+)-α-isopropyl-4-trifluoromethoxyphenylacetate By using the (+)-α-isopropyl-4-trifluoromethoxyphenylacetic acid and procedures of Examples 12 and 13, the product is obtained as pale yellow oil: $[\alpha]_D^{R.T.} = 6.1°$ (CHCl$_3$, C=5 g/100 ml).

EXAMPLE 54

Insecticidal Activity of α-cyano-m-phenoxybenzyl α-isopropyl-4-(trifluoromethoxy)phenylacetate The insecticidal activity of the compounds prepared from the acids of this invention is demonstrated in the following tests, wherein Tobacco budworm, *Heliothis virescens* (Fabricius); Western Potato Leafhopper, *Empoasca abrupta* DeLong and Bean Aphid, *Aphis fabae* (Scopoli), are employed as test insect species. Procedures employed are as follows:

Tobacco Budworm *Heliothis virescens* (Fabricius)

First Instar

A cotton plant with two true leaves expanded is dipped for 3 seconds with agitation in a test solution (35% water/65% acetone) containing 300, 100 or 10 ppm of test compound. Each leaf is placed in a cup with a wick and a piece of cheesecloth infested with 50-100 newly hatched larvae is added before covering the cup with a lid. After 3 days at 80° F., 50% r.h., the cups are examined and the kill of newly hatched larvae noted. Data obtained are reported as percent kill in Table I.

Bean Aphid, *Aphis fabae* (Scopoli)

Five cm fiber pots, each containing a nasturtium plant 2 inches high and infested with 100 to 150 aphids 2 days earlier are placed on a 4 rpm turntable and sprayed with a 35% water/65% acetone solution containing 100, 10, 1.0 and 0.1 ppm of test compound for 2 revolutions using a DeVilbiss Atomizer and 20 psi air pressure. The spray tip is held about 15 cm from the plants and the spray directed so as to give complete coverage of the aphids and the plants. The sprayed plants are laid on their sides on white enamel trays. Mortality estimates are made after 1 day at 70° F., 50% r.h.

Data are reported as percent mortality determined at the rate indicated (Table I).

Western Potato Leafhopper, *Empoasca abrupta* Delong

A Sieve lima bean plant with the primary leaf expanded to 3 to 4 inches is dipped into a 35% water/65% acetone solution containing 100, 10 or 1 ppm of test compound. The dipped plant is placed in the hood to dry and then a 2.5 cm piece of the tip of one leaf is cut off and placed in a 4-inch petri dish with a moist filter paper in the bottom. From 3 to 10 second-instar nymphs are placed in the dish and the dish is then covered. Mortality counts are made after holding the thus prepared dishes for 2 days at 80° F. and 50% r.h. Data obtained are reported in Table I.

$CHF_2$ or $CF_3$ and $R_2$ is ethyl, n-propyl, isopropyl, isopropenyl or t-butyl; or the optical isomers thereof.

2. A compound according to claim 1 wherein X is S or O, R is H or F and $R_2$ is isopropyl, n-propyl or ethyl.

3. A compound according to claim 2 where $R_2$ is isopropyl, X is O and Z and Y are hydrogen.

4. A compound according to claim 3:

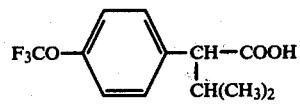

5. The (+)-isomer of claim 4.
6. A compound according to claim 3:

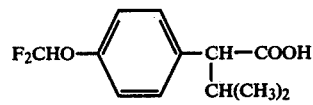

7. The (+)-isomer of claim 6.
8. A compound according to claim 2:

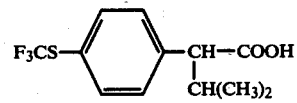

9. A compound according to claim 2:

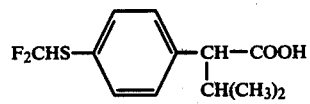

10. A compound according to claim 2:

TABLE I

| | Insecticidal Evaluation | | | | | | | | | |
|---|---|---|---|---|---|---|---|---|---|---|
| | % Mortality | | | | | | | | | |
| | Tobacco Budworm Larvae 1st Instar | | | Leafhopper | | | Aphids | | | |
| Compound | 300 ppm | 100 ppm | 10 ppm | 100 ppm | 10 ppm | 1 ppm | 100 ppm | 10 ppm | 1 ppm | 0.1 ppm |
| 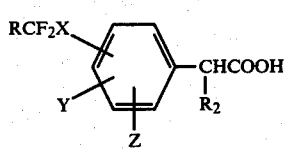 | 100 | 100 | 100 | 100 | 100 | 70 | 100 | 100 | 90 | 50 |

We claim:
1. A compound of the formula:

RCF₂X—⌬—CHCOOH with Y, Z substituents and R₂ wherein $RCF_2$, X, Y and Z are all meta or para to the carbon to the acid group; X is O, S, SO or $SO_2$; Y and Z are each H, Cl, F, Br, $NO_2$, $CH_3$ or $OCH_3$; R is H, F, 11. A compound according to claim 2:

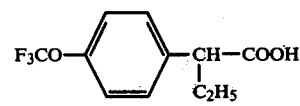

12. A compound according to claim 2:

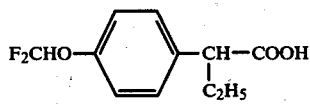

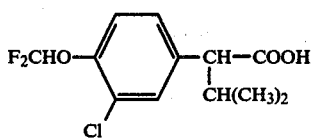
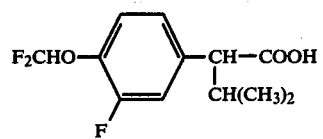
13. A compound according to claim 2:
* * * * *